United States Patent
Helbert et al.

(10) Patent No.: US 8,921,078 B2
(45) Date of Patent: Dec. 30, 2014

(54) METHOD FOR TRANSFORMING IOTA-CARRAGEENAN INTO ALPHA-CARRAGEENAN BY MEANS OF A NEW CLASS OF 4S-IOTA-CARRAGEENAN SULFATASE

(75) Inventors: William Helbert, Roscoff (FR); Aurelle Prechoux, Elliant (FR); Sabine Genicot-Joncour, Saint-pol-de-leon (FR)

(73) Assignee: Centre National de la Recherche Scientifique-CNRS, Paris Cedex (FR)

( * ) Notice: Subject to any disclaimer, the term of this patent is extended or adjusted under 35 U.S.C. 154(b) by 0 days.

(21) Appl. No.: 13/879,129

(22) PCT Filed: Oct. 17, 2011

(86) PCT No.: PCT/FR2011/052421
§ 371 (c)(1),
(2), (4) Date: Jul. 8, 2013

(87) PCT Pub. No.: WO2012/049437
PCT Pub. Date: Apr. 19, 2012

(65) Prior Publication Data
US 2013/0280765 A1    Oct. 24, 2013

(30) Foreign Application Priority Data

Oct. 15, 2010 (FR) .................................... 10 58420

(51) Int. Cl.
*C12P 19/04* (2006.01)
*C12N 9/16* (2006.01)

(52) U.S. Cl.
CPC ...................................... *C12P 19/04* (2013.01)
USPC .......................................... 435/101; 435/196

(58) Field of Classification Search
None
See application file for complete search history.

(56) References Cited

FOREIGN PATENT DOCUMENTS

WO    0068395 A2    11/2000

OTHER PUBLICATIONS

Préchoux et al., "Controlling Carrageenan Structure Using a Novel Formylglycine-Dependent Sulfatase, an Endo-4S-iota-Carrageenan Sulfatase", Mar Biotechnol (2013) 15:265-274.*
Ruth Falshaw et al.; Structural Analysis of Carrageenans From Burmese and Thai Samples of Catenella Nipae Zanardini; Carbohydrate Research, Pergamon, GB, vol. 285, May 14, 1996, pp. 81-98, XP004018644, ISSN: 0008-6215, DOI: 10-1016/0008-6215(96)00031-6.
Sabine Genicot-Joncour et al.; The Cyclization of the 3,6-Anhydro-Galactose Ring of Iota-Carrageenan Is Catalyzed by Two D-Galactose-2, 6-Sulfurylases in the Red Alga Chondrus Crispus; Plant Physiology, American Society of Plant Physiologists, Rockville, MD, US; vol. 151, No. 3; Nov. 1, 2009; pp. 1609-1616, XP002598802; ISSN: 0032-0889. DOI: 10-1104/ PP.109.144329.
Database UniProt (Online); Jul. 25, 2006; Subname: Full=Sulfatase; Flags: Precursor; XP002640183; retrieved from EBI accession No. UNIPROT:Q15XH3; Database accession No. Q15XH3.
Maitland W. McLean et al.; Glycosulphatase From *Pseudomonas Carrageenovora*, Purification and Some Properties; European Journal of Biochemistry, Blackwell Publishing, Berlin, DE; vol. 101, No. 2, Nov. 1, 1979; pp. 497-505, XP000961727; ISSN: 0014-2956, DOI: 10.1111/ J.1432-1033.1979.TB19744.X.
Gurvan Michel et al.; Bioconversion of Red Seaweed Galactans: A Focus on Bacterial Agarases and Carrageenases; Applied Microbiology and Biotechnology, Springer Vergla, Berlin, DE; vol. 71, No. 1, Jun. 1, 2006; pp. 23-33, XP002562259; ISSN: 0175-7598, DOI: 10-1007/S00253-006-0377-7.

* cited by examiner

*Primary Examiner* — Suzanne M Noakes
(74) *Attorney, Agent, or Firm* — Bachman & LaPointe, P.C.

(57) ABSTRACT

A method for transforming iota-carrageenan into alpha-carrageenan by a new class of 4S-iota-carrageenan sulfatase. The invention also relates to carrageenans obtained by the conversion method. The invention can be especially applied to the agro-food, pharmaceutical and cosmetic industries.

4 Claims, 4 Drawing Sheets

>Q15XH3
MTFNKKVSTLLWGTLIAISVGNASAADAGQSKADESNEKPNILFVLADDLGYNDVGF
NGSTDIKTPNLDGLAKNGMTFDAAYVAHPF*CGPSRAAIMTGR*YPHKIGAQFNLPED
NSNVGVSADELFIAQTMKSAGYFTGAMGKWHLGEASEYHPNKHGFDEFYGFLGG
GHNYFPEQFEAAYNKRVAQGMTNINMYLTPLEHNGKEVRETEYITDGLSREAVNFV
DKAAAKKKPFFLYLAYNAPHVPLQAKEEDMAMFSQIKDKKRRTYAGMVYAVDRGV
GRIVEQLKKNGQFDNTVIVFTSDNGGKLGQGANNYPLKEGKGSVQEGGFRTPMLV
HWPKHMKAGSRFSHPVLALDLYPTFAGLGGAVLPEDKKLDGKDIWADIQANTAPHK
DEFIYVLRHRNGYSDAAARRNQFKAVKNHNDDWKLYNIAQDISEDNDISAQHPDILR
DMVSSMESWSWNNQQPKWFHQSAEGAQWRLKAMPRFDQTFQVGDNTRSNSKK
GH

Figure 5

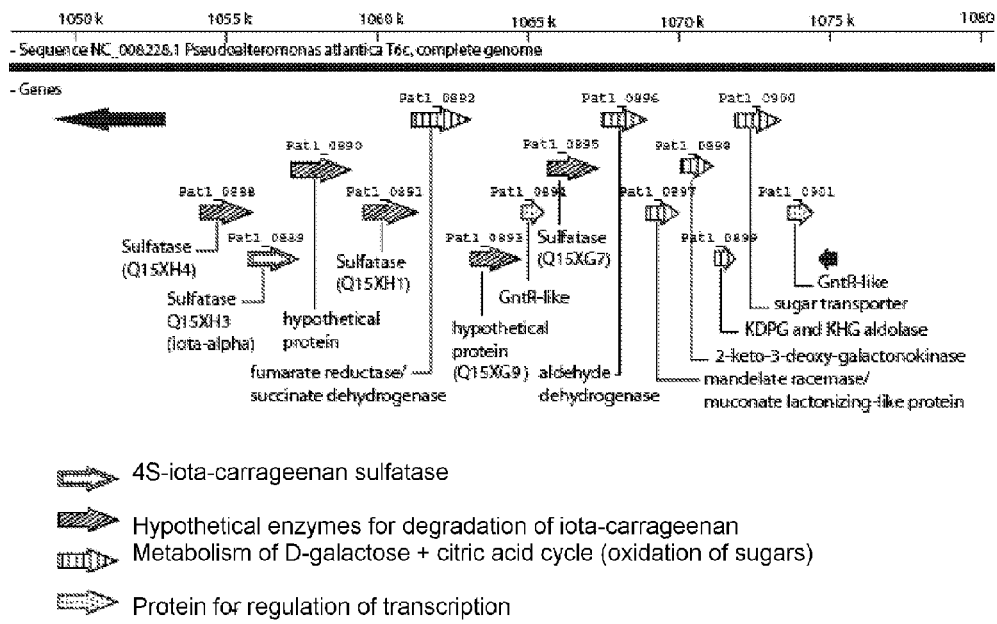

→ 4S-iota-carrageenan sulfatase

→ Hypothetical enzymes for degradation of iota-carrageenan

→ Metabolism of D-galactose + citric acid cycle (oxidation of sugars)

→ Protein for regulation of transcription

Figure 6

METHOD FOR TRANSFORMING IOTA-CARRAGEENAN INTO ALPHA-CARRAGEENAN BY MEANS OF A NEW CLASS OF 4S-IOTA-CARRAGEENAN SULFATASE

BACKGROUND

1. Technical Field

The present invention relates to a method for transforming iota-carrageenan to alpha-carrageenan by means of a novel class of 4S-iota-carrageenan sulfatase. The present invention also relates to carrageenans obtained by said conversion method.

The present invention finds application especially in the agro-food, pharmaceutical and cosmetic industries.

In the description below, the references in square brackets ([ ]) refer to the list of references presented at the end of the text.

2. State of the Art

Carrageenans are sulfated galactans extracted from the wall of marine red algae. Carrageenans are composed of a succession of D-galactosides alternately linked by alpha(1-3) and beta(1-4) bonds. These anionic polysaccharides are mainly distinguishable by the presence or otherwise of a 3,6 anhydro bridge on the galactose residue linked at the alpha (1-3) position, and by their degree of sulfation. For example, the three disaccharide repeating units—called carrabiose motif—found in the most industrially exploited carrageenans are characterized by the presence of one (kappa-carrabiose), two (iota-carrabiose) or three sulfates (lambda-carrabiose) (FIG. 1). Carrageenans may be mainly composed of a carrabiose motif, for example kappa-carrageenan from the alga *Kappaphycus alvarezzi* is composed of about 90% kappa-carrabiose motif and 10% iota-carrabiose. The iota-carrageenan extracted from *Eucheuma denticulatum* is composed of 85% iota-carrabiose units and 15% kappa-carrabiose units.

The compositions with respect to carrabiose unit may be highly variable and depend mainly on the botanic origin of the alga. The term kappa-carrageenan is used when the polysaccharide is rich in kappa-carrabiose motif and when these physicochemical properties are similar to those of kappa-carrageenan from *K. alvarezzi* which is often used as reference (Bixler et al., Food Hydrocolloids, 15: 619-630, 2001) [1].

A whole range of intermediate structures of hybrid kappa/iota-carrageenans has been described according to the botanic origin of the polysaccharides (FIG. 2; Bixler et al., 2001, cited above) [1]. The type of carrageenan present in the wall of algae may also be correlated with the stage of life of the algae. Indeed, in the case of *Chondrus crispus*, the gametophytes are rich in kappa/iota-carrageenans while the sporophytes contain mainly lambda-carrageenan. The seasons and all the environmental factors which may affect the growth of algae (illumination, temperature, salts and the like) will also have an effect on the carrageenan structure and composition. Consequently, depending on the origin and/or the procedures for extraction, a wide range of structures of the kappa-, iota- and lambda-carrageenan type may be observed.

These polysaccharides have unique rheological properties and are used as texturing agents in the agro-food, pharmaceutical and cosmetic industries. These polysaccharides have a wide range of functional properties which can be explained by their high structural diversity. The kappa- and iota-carrageenans have the property of forming ion- and thermo-dependent gels. Kappa-carrageenan will form rigid gels in the presence of potassium while iota-carrageenan forms flexible and elastic gels in the presence of calcium. The high diversity of chemical structure of carrageenans and their natural hybridity confer characteristic functional properties on each alga extract.

About 50 000 tons of carrageenans are sold yearly (Bixler and Porse, J. Appl. Phycol., 2010, online) [2]. However, the tonnage of carrageenans exploited is limited by the quantity of red alga available. Currently, two species of red alga are widely cultivated: *Kappaphycus alvarezzi* and *Eucheuma denticulatum* from which kappa- and iota-carrageenan are extracted, respectively. Numerous wild algae (not cultivated) are also collected in a large quantity because their carrageenans, of a kappa/iota-hybrid nature, exhibit highly advantageous functional properties. However, a ton of these algae is twice or even ten times more expensive than that of cultivated algae.

In addition, each industrial application corresponds to extracts of carrageenans obtained from one species or from several species of red algae. The solutions for satisfying the industrial needs in any field reside mainly in the formulation (mixture) of carrageenans (Bixler and Porse, 2010, cited above) [2].

Consequently, a biotechnological process which would make it possible to obtain hybrid carrageenans from cultivated algae would be economically highly profitable. It would have the advantage of being less dependent on the source of algae, and would open novel perspectives for the exploitation and upgrading of the biomass of red algae.

In order to control the chemical structure and, by extension, the physicochemical properties of carrageenans, the inventors therefore undertook the purification and the production of enzymes capable of modifying and correcting the structures of carrageenans. The desired modifications consist of the desulfation of carrageenans by enzymes called sulfatases which lead to the conversion of iota- to kappa- or alpha-carrageenan, or to hybrid structures of the kappa/iota- or iota/alpha-carrageenan type (FIG. 3). They thus demonstrated the existence of carrageenan sulfatases which can act directly on the polymer without preliminary action of carragenases. They succeeded in purifying, from a bacterial population *Pseudoalteromonas carrageenovora*, a first 4S-iota-carrageenan sulfatase belonging to the family of amidohydrolases and which converts iota- to alpha-carrageenan by specific desulfation (removal of an $SO_3^-$ group) at the 4 position of iota-carrageenan (French patent application FR 09/52642) [3]. Using the same strategy as for the first 4S-iota-carrageenan sulfatase, the inventors succeeded in purifying, from *Pseudoalteromonas atlantica*, a second 4S-iota-carrageenan sulfatase belonging to the family of formylglycin-dependent sulfatases. They first of all succeeded in determining three peptides of said protein: NGQFDNTVIVFTSDNGGK (SEQ ID NO:1), FDQTFQVGDNTR (SEQ ID NO:2), and ETEYITDGLSR (SEQ ID NO:3), which, once compared with the TrEMBL library, demonstrated a correspondence with the Q15XH3 protein of *P. atlantica* T6c whose gene (Patl_0889) was labeled a sulfatase (ProteinJD ABG39415.1; Copeland et al., 2006) [4].

The 4S-iota-carrageenan sulfatases could therefore make it possible to calibrate the "hybridity" of carrageenans. Thus, any sulfatase acting on iota-carrageenan could represent a major innovation because it would make it possible to manufacture alpha- and iota/alpha-carrageenans which are very scarce in nature, and which are different in terms of peptide sequence but also in terms of biochemical properties. However, it appeared that it was possible for sulfatases acting on carrageenans not to exhibit homology with the other sulfatases known—the most widely studied sulfatases being the enzymes acting on heparine, a polysaccharide of animal origin.

A real need therefore exists for purifying enzymes for modifying the motifs of sulfation of carrageenans in order to overcome the deficiencies, disadvantages and obstacles of the prior art, in particular for a method which makes it possible to control the "hybridity" of carrageenans using said enzymes, to reduce the costs and to control the supply and the functional properties of the carrageenans thus obtained.

SUMMARY

The inventors have demonstrated, quite unexpectedly, that the second 4S-iota-carrageenan sulfatase identified (Q15XH3) is capable of converting the iota-carrabiose motif to the alpha-carrabiose motif. The iota-carrabiose motif may be present in an oligosaccharide or a polysaccharide which may also be composed of other carrabiose motifs.

The subject of the present invention is therefore a method for transforming iota-carrageenan to alpha-carrageenan comprising the enzymatic catalysis of the conversion of the iota-carrabiose motif to the alpha-carrabiose motif by an enzyme whose peptide sequence comprises the peptides having the following sequences:

```
                              (SEQ ID NO: 1)
NGQFDNTVIVFTSDNGGK, (SEQ ID NO: 2)
FDQTFQVGDNTR,
and (SEQ ID NO: 3)
ETEYITDGLSR.
```

The expression "iota- and alpha-carrageenan" is understood to mean, for the purposes of the present invention, iota- and alpha-carrageenans and/or hybrid iota- and alpha-carrageenans, for example contained in solution, a partially gelled solution or a gel. Thus, pure iota-carrageenan gels under its own charges, while hybrid carrageenans such as iota-nu-carrageenan and oligo-iota-carrageenans are poorly gel-forming.

According to a particular embodiment of the method of the invention, said enzyme has the following peptide sequence:

```
                                               (SEQ ID NO: 4)
MTFNKKVSTLLWGTLIAISVGNASAADAGQSKADESNEKPNILFVLA

DDLGYNDVGFNGSTDIKTPNLDGLAKNGMTFDAAYVAHPFCGPSRAA

IMTGRYPHKIGAQFNLPEDNSNVGVSADELFIAQTMKSAGYFTGAMG

KWHLGEASEYHPNKHGFDEFYGFLGGGHNYFPEQFEAAYNKRVAQGM

TNINMYLTPLEHNGKEVRETEYITDGLSREAVNFVDKAAAKKKPFFL

YLAYNAPHVPLQAKEEDMAMFSQIKDKKRRTYAGMVYAVDRGVGRIV

EQLKKNGQFDNTVIVFTSDNGGKLGQGANNYPLKEGKGSVQEGGFRT

PMLVHWPKHMKAGSRFSHPVLALDLYPTFAGLGGAVLPEDKKLDGKD

IWADIQANTAPHKDEFIYVLRHRNGYSDAAARRNQFKAVKNHNDDWK

LYNIAQDISEDNDISAQHPDILRDMVSSMESWSWNNQQPKWFHQSAE

GAQWRLKAMPRFDQTFQVGDNTRSNSKKGH.
```

According to a particular embodiment of the method of the invention, said enzyme is a 4S-iota-carrageenan sulfatase. For example, it may be a 4S-iota-carrageenan sulfatase having a sequence exhibiting at least 30% sequence identity with SEQ ID NO: 4, preferably at least 50% sequence identity with SEQ ID NO: 4, most preferably at least 80% with SEQ ID NO: 4.

According to a particular embodiment of the method of the invention, the enzyme is produced by a host cell comprising a nucleic acid encoding said enzyme and/or a vector comprising a nucleic acid sequence encoding said enzyme.

The expression "host cell" is understood to mean, for the purposes of the present invention, a prokaryotic or eukaryotic cell. Host cells commonly used for the expression of recombinant cells include in particular cells of bacteria such as *Escherichia coli* or *Bacillus*, cells of yeasts such as *Saccharomyces cerevisiae*, cells of fungi such as *Aspergillus niger*, cells of insects, and cells of mammals (in particular humans) such as the cell lines CHO, HEK 293, PER-C6, and the like. The transformation of prokaryotic and eukaryotic cells is a technique well known to a person skilled in the art, for example lipofection, electroporation, heat shock, or chemical methods. Depending on the cell to be transformed, persons skilled in the art can easily determine the means necessary for the introduction and expression of the nucleic acid in the chosen host cell. Thus, the expression vector and the method of introduction of the expression vector into the host cell will be selected according to the chosen host cell. The host cell transformed with an expression vector or a nucleic acid will express the corresponding polypeptide in a stable manner. Persons skilled in the art can easily check that the host cell expresses the polypeptide in a stable manner, for example using the Western blot technique.

The expression "vector" is understood to mean, for the purposes of the present invention, vectors for the expression and/or secretion of nucleic acid sequences in a given host cell. They may be for example vectors of plasmid or viral origin containing, in addition to the nucleic acid sequence, the means necessary for its expression. These means may for example include a promoter, signals for initiation and termination of translation, as well as appropriate regions for regulation of transcription. The expression vector may also comprise other elements such as a replication origin, a multiple cloning site, an enhancer, a signal peptide which may be fused in phase with the polypeptide produced during cloning, and one or more selectable markers.

The expression "nucleic acid" is understood to mean, for the purposes of the present invention, both DNA molecules and RNA molecules, which includes in particular cDNA molecules and mRNA molecules. The nucleic acid may be in double-stranded form (for example in the case of a nucleic acid contained in an expression vector) or in single-stranded form (for example in the case of probes or primers).

The subject of the present invention is also carrageenans which may be obtained by the method of the invention.

According to a particular embodiment of the method of the invention, the carrageenans obtained have alpha-carrabiose motifs as long as the starting carrageenan had iota-carrabiose motifs in its structure. For example, the iota-carrabiose motifs of the carrageenan extracted from *E. denticulatum* (85% iota-carrabiose and 15% kappa-carrabiose) may be converted to a carrageenan having 85% alpha-carrabiose and 15% kappa-carrabiose. The enzymatic reaction may be controlled and the rate of conversion of iota-carrabiose to alpha-carrabiose may vary from 0 to 100%. The rheological properties of the carrageenans obtained will vary according to the rate of conversion.

Other advantages may also be apparent to a person skilled in the art on reading the examples below, illustrated by the accompanying figures given as a guide.

BRIEF DESCRIPTION OF THE DRAWINGS

FIG. 5 represents the amino acid sequence of the *Pseudoalteromonas atlantica* T6c protein (Q15XH3). In bold, the three peptide sequences determined by mass spectrometry. In italics and underlined, the signature for the post-translational modification of cystein. Boxed, the amino acids of the catalytic site including lysine (K) and histidine (H) which are the catalytic amino acids.

FIG. 6 represents the genomic environment of the gene for the novel 4S-iota-carrageenan sulfatase (Q15XH3) in *P. atlantica*.

DETAILED DESCRIPTION

Example 1

Figure 1:
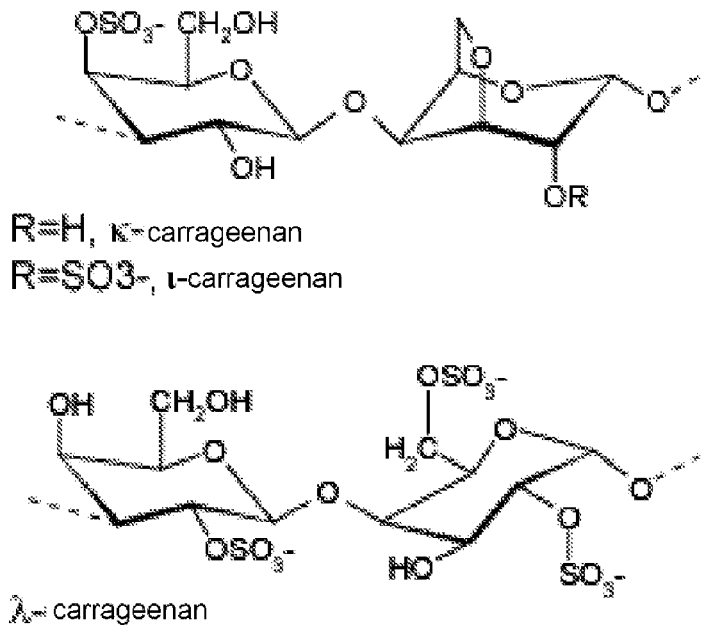
FIG. 1 represents the chemical structure of the repeating motifs of the three main carrageenans (kappa κ, iota ι, and lambda λ) industrially exploited.
Figure 2:
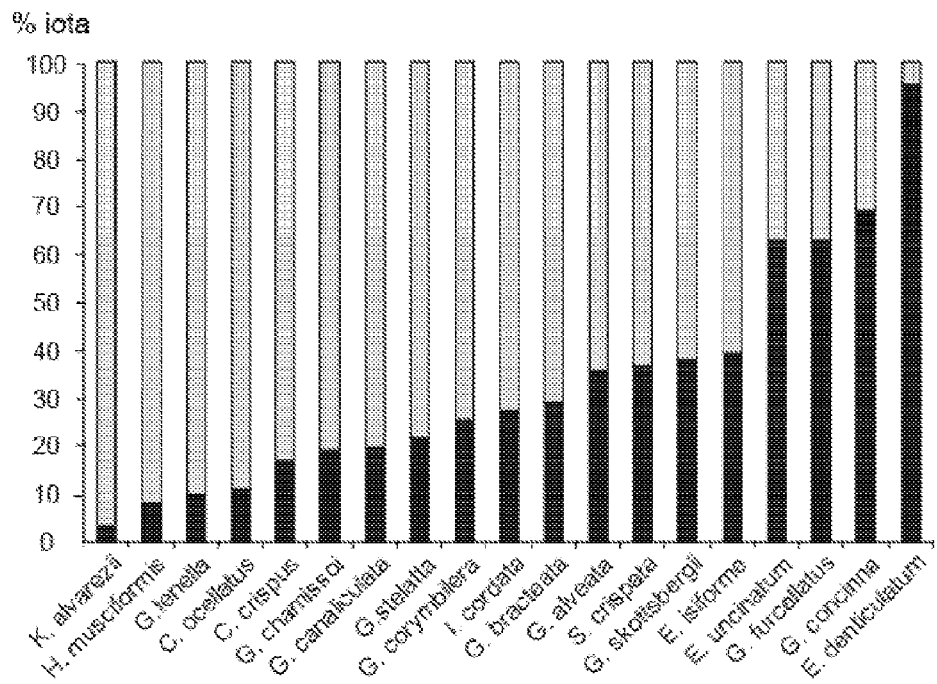
FIG. 2 represents the hybrid kappa/iota-carrageenan compositions as a function of the source of red algae (Bixler et al., 2001, cited above) [1].
Figure 3:
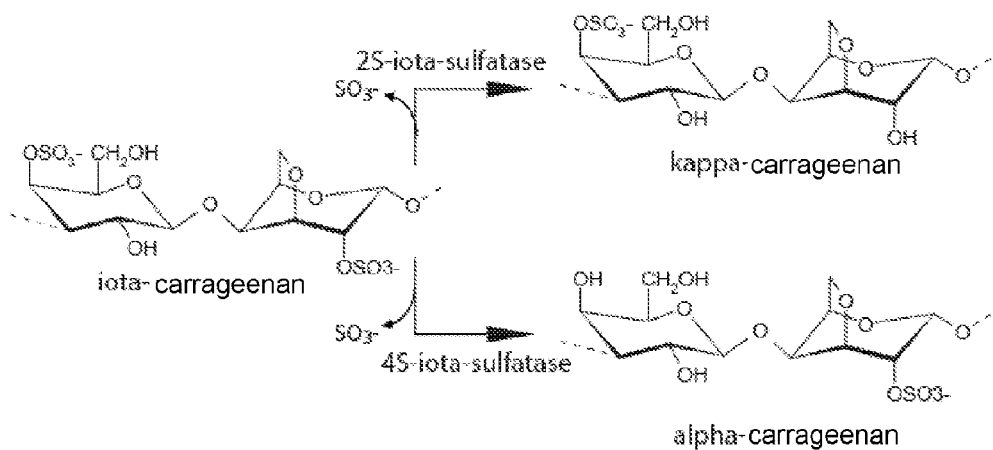
FIG. 3 represents the diagram for the enzymatic reactions catalyzed by 4S- and 2S-iota-carrageenan sulfatases.

Identification of a Novel 4S-Iota-Carrageenan Sulfatase Obtained from *Pseudoalteromonas atlantica*

Screening of the Carrageenan Sulfatase Activities of *Pseudoalteromonas atlantica*

The screening was carried out using the marine bacteria *Pseudoalteromonas atlantica* T6c (ATCC T6c/BAA-1087 strain) whose genome has been completely sequenced.

Bacterial Cultures

The production of bacterial extracts was carried out using the marine bacterium *Pseudoalteromonas atlantica* cultured in Zobell medium [Bactopeptone (Amresco) 5 g/l, yeast extracts (BD, Extract of Autolysed Yeast cells) 1 g/l, filtered sea water 800 ml adjusted to 1 l with demineralized water] in the presence of kappa- (*Kappaphycus alvarezii*, CP Kelco X6913, at 1 g/l), of iota- (*Eucheuma denticulatum*, H030058-534, at 1 g/l) or of lambda-carrageenan (sporophyte of *Gigartina skottsbergii*, CP Kelco, X7055).

The first preculture consisted in inoculating 10 ml of Zobell medium from a glycerol of *P. atlantica* stored at −80° C. The incubation was carried out in a New Brunswick type shaker for 36 h, at 18° C. and 180 rpm. For the second preculture, 50 ml of Zobell medium containing 50 mg of one of the carrageenans (kappa-, iota- or lambda-) were inoculated with about 1 ml of the first preculture, so as to have an absorbance of 0.1, at 660 nm. This second preculture was incubated at 18° C. until the optical density reaches a value of 1 to 1.2, at 660 nm, that is about 8 h. For the final culture, 950 ml of Zobell medium containing the same carrageenan as before were inoculated with the 50 ml of the second preculture, and incubated at 18° C. for 36 h.

In order to separate the bacterial pellet from the culture supernatant, the bacterial cultures were centrifuged at 6200 g for 20 minutes, at 4° C.

Preparation of the Bacterial Extracts

The culture supernatant is concentrated by precipitation at 90% saturation with ammonium sulfate (61.5 g of ammonium sulfate per 100 ml of sample). The pellet obtained after centrifugation (25 min, 10 000 rpm) is put back into solution in 50 mM Tris-HCl buffer pH 8.3. It is then dialyzed in membranes (Spectra/por, MWCO 3500 Da) against 50 mM Tris-HCl buffer pH 8.3.

The bacterial pellet was resuspended in 50 mM Tris-HCl buffer (Sigma) at pH 8.3. The cells were then lyzed in a French press, and the lysate obtained was ultracentrifuged at 27 000 g, for 2 h 45 min. Half a tablet of antiprotease (Complete, EDTA-free, Roche) was added to the supernatant obtained.

The extract was then dialyzed (Spectra/Por, MWCO 3500 Da) against 50 mM Tris-HCl buffer at pH 8.5 overnight with stirring at 4° C.

Assaying of the Sulfate Released

The production of the sulfatase activities was evaluated by means of measuring the quantity of sulfate released after incubation of various carrageenans in the presence of bacterial extracts. The assays were carried out with the concentrated culture supernatants and the bacterial pellets. For each sample analyzed, a blank is prepared in a similar manner after having inactivated the enzymatic extract beforehand for about fifteen minutes at 100° C.

The reaction media were diluted 2-fold with milliQ water (Millipore) and then centrifuged in microcons (Amicon) with a cut-off of 10 kDa. This centrifugation was carried out at 3300 g for 90 min at room temperature. The filtrate obtained was then assayed by anion-exchange chromatography (HPAEC: High Performance Anion Exchange Chromatography) on a Dionex system. Twenty μl of sample were injected using an automatic injector (AS3000, Thermo). The separation of the anions present in the samples was carried out using an Ion-Pac AS11 column (4×200 mm, Dionex) provided with an AG-1 1 precolumn (4×50 mm, Dionex). The system was equilibrated with respect to 12 mM NaOH. The elution was carried out using an NaOH isocratic gradient at a flow rate of 1 ml/min (GP40 pump, Dionex). The detection of the anions was carried out by conductimetry with an ED40 detector (Dionex) provided with an ASRS ultra-II-4 mm suppressor (Dionex) operating at a current of 198 mA. The software used for data acquisition and processing was the Chroméléon 6.8 software. Using a calibration curve, the area of the sulfate peaks was converted to parts per million (ppm). The difference between the value for the sample and that for the blank gave the quantity of sulfate released in ppm during the enzymatic desulfation reaction. The results are presented in table 1 below.

TABLE 1

| Bacterial extract | Induction | Substrate | | | | |
|---|---|---|---|---|---|---|
| | | kappa | iota | lambda | kappa/mu | iota/nu |
| Supernatant | kappa | 0.22 | 0 | 0.04 | 0.08 | 0.28 |
| | iota | 1.36 | 39.36 | 1.26 | 21.96 | 18.96 |
| | lambda | 0.26 | 3.24 | 0.74 | 0.1 | 5.76 |
| Pellet | kappa | 0.04 | 3.4 | 0.08 | 0.4 | 4.28 |
| | iota | 4.5 | 80.82 | 3.64 | 8.94 | 63.58 |
| | lambda | 0.36 | 12.9 | 0.04 | 1.08 | 17.3 |

The results in bold correspond to the conditions for which the highest sulfatase activities were observed.

Purification and Protein Sequence of a Novel 4S-Iota-Carrageenan Sulfatase

Preparation of the Bacterial Extract

The bacterial pellet obtained from the culture induced with iota-carrageenan and obtained as previously described, containing the sulfatase activity, was resuspended in 50 mM Tris-HCl buffer (Sigma) at pH 7.5. The cells were then lyzed using a French press and the lysate obtained was ultracentrifuged at 27 200 g for 2 h 45 min. Half a tablet of antiprotease (Complete, EDTA-free, Roche) was added to the supernatant obtained in order to limit the degradation of the proteins.

In order to remove the small-size molecules (and in particular the free sulfate) from the extract, the latter was dialyzed (Spectra/Por, MWCO 3500 Da) against 50 mM Tris-HCl buffer at pH 7.5 overnight with stirring at 4° C.

Purification

The purification experiments were carried out on sulfatases acting on iota-carrageenan. The purification steps were carried out using an Akta Purifier system.

The lysate was deposited on a weak anion-exchange chromatography column DEAE Sepharose Fast Flow (GE Healthcare—45×1 cm) equilibrated beforehand in 50 mM Tris-HCl buffer at pH 7.5. The sample (about 35 ml) was loaded using a superloop (or injection loop) at a flow rate of 2 ml/min. The resin was then washed with this same buffer until a negligible absorbance was obtained at 280 nm. The elution of the proteins was carried out at a flow rate of 2 ml/min with a segmented, increasing NaCl gradient of 0 to 1M: 10 column volumes of 0 to 500 mM NaCl and 2 column volumes of 500 mM to 1M NaCl. The collected fractions with a volume of 5.5 ml were tested for their capacity to desulfate iota-carrageenan.

A fraction containing a maximum sulfatase activity was then dialyzed (Spectra/Por membrane, MWCO 3500 Da) for 48 h against 50 mM Tris-HCl buffer at pH 7.5, with stirring at 4° C. 1 ml of this fraction was deposited on a strong anion-exchange resin Q Fast Flow (GE Healthcare—Hitrap 1 ml) equilibrated beforehand in 50 mM Tris-HCl buffer at pH 7.5. The resin was washed with this same buffer and the proteins were eluted with an increasing NaCl gradient from 0 to 1M made in the following manner: 15 column volumes of 0 to 500 mM NaCl and 5 column volumes of 500 mM to 1M NaCl, at a flow rate of 1 ml/min. The collected fractions of 1 ml were incubated in the presence of iota-carrageenan in order to measure the sulfatase activity. The degree of purity of the fractions was visualized by SDS-PAGE polyacrylamide gel electrophoresis.

Figure 4:
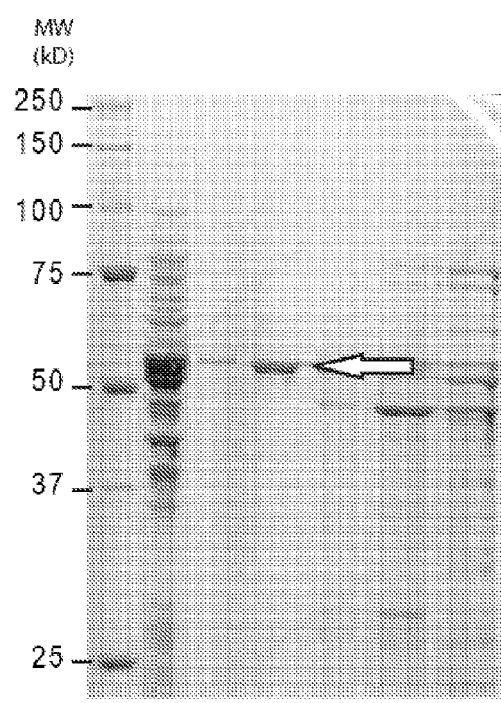
FIG. 4 represents colloidal Coomassie blue stained electrophoretic gel (SDS-PAGE) of several fractions collected after the anion-exchange chromatography step (Q Sepharose Fast Flow). The 55 kDa protein is shown by an arrow.

The purity of the active fractions was analyzed by SDS-PAGE polyacrylamide gel electrophoresis (Biorad, Criterion XT 12% Bis-Tris). To 15 µl of sample, were added 5 µl of loading buffer containing 2% SDS (Amresco), 5% β-mercaptoethanol (98% Sigma), 20% glycerol (CarloErba), 62.5 mM Tris-HCl at pH 6.8 and 0.5% Bromophenol blue (Sigma). The samples were then heated at boiling temperature for 3 min in order to denature the proteins. The 20 µl of mixture were then deposited on the gel. The depositions of 5 µl of size markers (Biorad, Precision Plus Protein) made it possible to evaluate the molecular weight of the proteins between 10 and 250 kDa. The migration was carried out at room temperature, at 110 volts (for 1 gel) for 2 h, in a migration buffer composed of 200 mM MOPS (Sigma), 250 mM Tris pH 8.1 and 5 g/l SDS. The visualization of the gel was carried out using colloidal Coomassie blue staining (Candiano et al., Electrophoresis, 25(9): 1327-1333, 2004) [5]. The molecular weight of the purified protein was estimated at about 55 kDa (FIG. 4).

Protein and Nucleic Sequence

The protein band was cut out of the gel, digested with trypsine and the peptides obtained were sequenced by mass spectrometry on the "Biopolymers" RIO platform located at INRA, Nantes. The three sequences determined [NGQFDNTVIVFTSDNGGK (SEQ ID NO: 1), FDQTFQVGDNTR (SEQ ID NO: 2), and ETEYITDGLSR (SEQ ID NO: 3)] were compared with the TrEMBL library. The three peptides correspond at 100% to the Q15XH3 protein (FIG. 5, SEQ ID NO: 4) of *Pseudoalteromonas atlantica* T6c whose gene (Patl_0889) was labeled as a sulfatase (Copeland et al., 2006, cited above) [4]. The protein has the consensus sequence of 12 amino acids (C/S-X-P-S/X-R-XXX-L/X-G/X-R/X, SEQ ID NO: 5) required for the conversion of cystein to formylglycine (FGly) and the catalytic amino acids present in the conserved sequence (G-Y/V-X-S/T-XXX-G-K-X-X-H, SEQ ID NO: 6). The genomic environment of the gene for the novel sulfatase points toward an involvement of this protein in the degradation of iota-carrageenan (FIG. 6). Indeed, the gene for Q15XH3 is located in a gene cluster which contains other sulfatases (including Q15XG7 which has 41% identity with Q15XH3), two unknown proteins, but especially several genes of the citric cycle (oxidation of sugars) and for the metabolism of D-galactose are clearly identified. The functions of the sulfatases present in this cluster are probably linked to the desulfation of iota- and/or alpha-carrageenan.

Sulfatase Activity

In order to measure the sulfatase activity, 100 µl of sample to be assayed were brought into contact with 100 µl of a solution of iota-carrageenan (CP-Kelco No. 1256) at 1% in 50 mM Tris-HCl buffer at pH 7.5. The enzymatic reactions were carried out at 34° C. in a water bath for 48 h. For each sample, a blank was prepared under similar conditions having inactivated beforehand the enzymatic extract for 15 min at 100° C.

Figure 7:
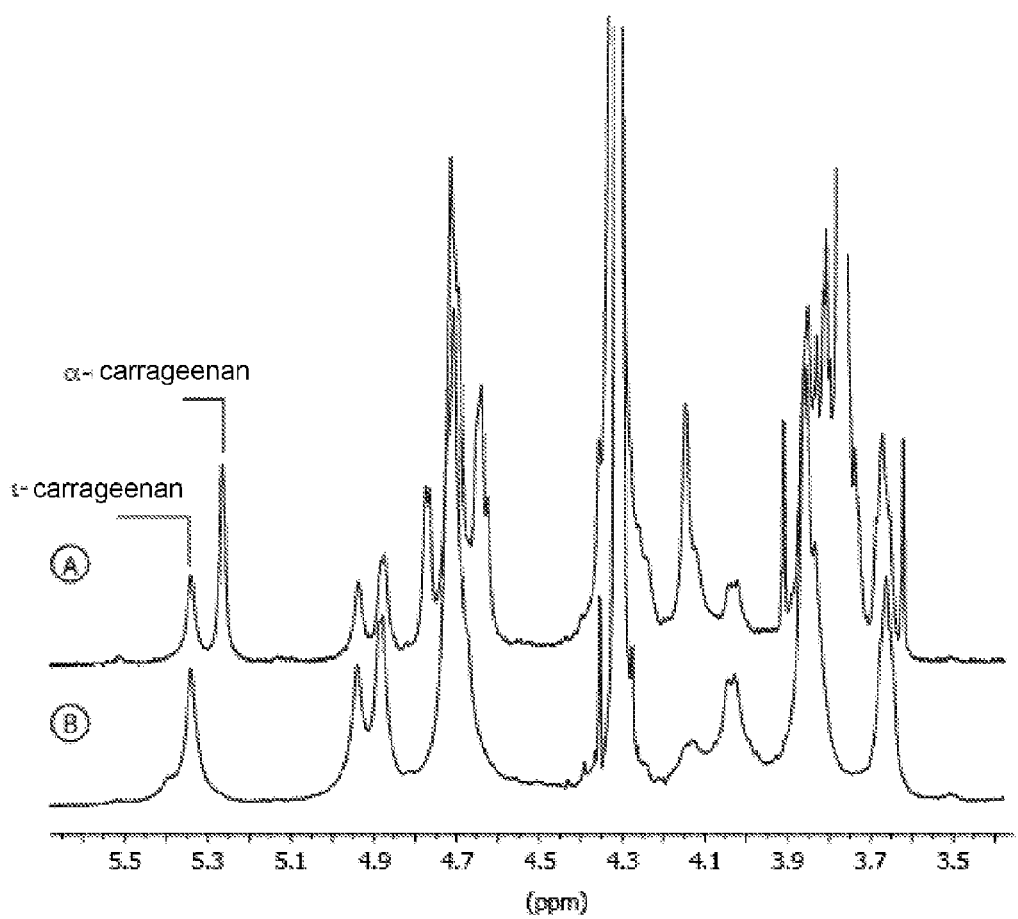
FIG. 7 represents the $^1$H NMR spectrum of iota-carrageenan (B) incubated with the purified protein from *Pseudoalteromonas atlantica* (Q15XH3) (A).

The position of the sulfated group cleaved and therefore the identification of the product formed during the enzymatic hydrolysis was carried out by NMR. For this analysis, the desulfation reactions were carried out by incubating 700 µl of 1 iota-carrageenan (CP-Kelco No. 1256) in the presence of 300 µl of bacterial extract. The reaction mixtures were incubated at 34° C. in a water bath for 72 h and then freeze-dried. The samples were then exchanged twice in $D_2O$ and then redissolved in 700 µl of $D_2O$ at 99.97% so as to arrive at an approximate concentration of 10 mg/ml. The $^1H$ NMR spectra were recorded at 70° C. on a BRUKER Avance DRX 500 spectrophotometer by the NMR department (Université de Bretagne Occidentale, Brest). The anomeric protons of the carrageenans exhibit characteristic chemical shifts (d) between about 5 and 5.6 ppm. The results show that the desulfation of iota-carrageenan by the pure protein led to the production of alpha-carrageenan (FIG. 7A), as in the case of the first purified 4S-iota-carrageenan sulfatase but whose molecular weight was 115 kDa (French patent application FR 09/52642, cited above) [3].

A novel sulfatase capable of converting iota- to alpha-carrageenan has therefore been identified. It is distinguishable from the sole 4S-iota-carrageenan sulfatase known to date which belongs to the family of amidohydrolases.

The sequence of the novel carrageenan sulfatase (Q15XH3) shows that it belongs to the family of FGly-sulfatases. This FGly-sulfatase is the first carrageenan sulfatase of this family which contains other enzymes acting on carbohydrates. Sulfatases acting on glycosaminoglycans (i.e. heparin) and cerebrosides have been described.

LIST OF REFERENCES

1. Bixler et al., Food Hydrocolloids, 15: 619-630, 2001
2. Bixler and Porse, J. Appl. Phycol., 2010, online
3. French patent application FR 09/52642
4. Copeland et al., "Complete sequence of *Pseudoalteromonas atlantica* T6c", EMBL ACCESSION No. CP000388, PROTEINJD ABG39415.1, 2006
5. Candiano et al., Electrophoresis, 25(9): 1327-1333, 2004

---

SEQUENCE LISTING

```
<160> NUMBER OF SEQ ID NOS: 6

<210> SEQ ID NO 1
<211> LENGTH: 18
<212> TYPE: PRT
<213> ORGANISM: Pseudoalteromonas atlantica

<400> SEQUENCE: 1

Asn Gly Gln Phe Asp Asn Thr Val Ile Val Phe Thr Ser Asp Asn Gly
1               5                   10                  15

Gly Lys

<210> SEQ ID NO 2
<211> LENGTH: 12
<212> TYPE: PRT
<213> ORGANISM: Pseudoalteromonas atlantica

<400> SEQUENCE: 2

Phe Asp Gln Thr Phe Gln Val Gly Asp Asn Thr Arg
1               5                   10

<210> SEQ ID NO 3
<211> LENGTH: 11
<212> TYPE: PRT
<213> ORGANISM: Pseudoalteromonas atlantica

<400> SEQUENCE: 3

Glu Thr Glu Tyr Ile Thr Asp Gly Leu Ser Arg
1               5                   10

<210> SEQ ID NO 4
<211> LENGTH: 500
<212> TYPE: PRT
<213> ORGANISM: Pseudoalteromonas atlantica

<400> SEQUENCE: 4

Met Thr Phe Asn Lys Lys Val Ser Thr Leu Leu Trp Gly Thr Leu Ile
1               5                   10                  15

Ala Ile Ser Val Gly Asn Ala Ser Ala Ala Asp Ala Gly Gln Ser Lys
            20                  25                  30

Ala Asp Glu Ser Asn Glu Lys Pro Asn Ile Leu Phe Val Leu Ala Asp
        35                  40                  45

Asp Leu Gly Tyr Asn Asp Val Gly Phe Asn Gly Ser Thr Asp Ile Lys
    50                  55                  60

Thr Pro Asn Leu Asp Gly Leu Ala Lys Asn Gly Met Thr Phe Asp Ala
65                  70                  75                  80

Ala Tyr Val Ala His Pro Phe Cys Gly Pro Ser Arg Ala Ala Ile Met
                85                  90                  95

Thr Gly Arg Tyr Pro His Lys Ile Gly Ala Gln Phe Asn Leu Pro Glu
            100                 105                 110

Asp Asn Ser Asn Val Gly Val Ser Ala Asp Glu Leu Phe Ile Ala Gln
        115                 120                 125

Thr Met Lys Ser Ala Gly Tyr Phe Thr Gly Ala Met Gly Lys Trp His
    130                 135                 140
```

Leu Gly Glu Ala Ser Glu Tyr His Pro Asn Lys His Gly Phe Asp Glu
145                 150                 155                 160

Phe Tyr Gly Phe Leu Gly Gly Gly His Asn Tyr Phe Pro Glu Gln Phe
            165                 170                 175

Glu Ala Ala Tyr Asn Lys Arg Val Ala Gln Gly Met Thr Asn Ile Asn
        180                 185                 190

Met Tyr Leu Thr Pro Leu Glu His Asn Gly Lys Glu Val Arg Glu Thr
    195                 200                 205

Glu Tyr Ile Thr Asp Gly Leu Ser Arg Glu Ala Val Asn Phe Val Asp
210                 215                 220

Lys Ala Ala Lys Lys Pro Phe Phe Leu Tyr Leu Ala Tyr Asn
225                 230                 235                 240

Ala Pro His Val Pro Leu Gln Ala Lys Glu Glu Asp Met Ala Met Phe
                245                 250                 255

Ser Gln Ile Lys Asp Lys Lys Arg Thr Tyr Ala Gly Met Val Tyr
            260                 265                 270

Ala Val Asp Arg Gly Val Gly Arg Ile Val Glu Gln Leu Lys Lys Asn
            275                 280                 285

Gly Gln Phe Asp Asn Thr Val Ile Val Phe Thr Ser Asp Asn Gly Gly
290                 295                 300

Lys Leu Gly Gln Gly Ala Asn Asn Tyr Pro Leu Lys Glu Gly Lys Gly
305                 310                 315                 320

Ser Val Gln Glu Gly Gly Phe Arg Thr Pro Met Leu Val His Trp Pro
                325                 330                 335

Lys His Met Lys Ala Gly Ser Arg Phe Ser His Pro Val Leu Ala Leu
            340                 345                 350

Asp Leu Tyr Pro Thr Phe Ala Gly Leu Gly Gly Ala Val Leu Pro Glu
        355                 360                 365

Asp Lys Lys Leu Asp Gly Lys Asp Ile Trp Ala Asp Ile Gln Ala Asn
        370                 375                 380

Thr Ala Pro His Lys Asp Glu Phe Ile Tyr Val Leu Arg His Arg Asn
385                 390                 395                 400

Gly Tyr Ser Asp Ala Ala Ala Arg Arg Asn Gln Phe Lys Ala Val Lys
                405                 410                 415

Asn His Asn Asp Asp Trp Lys Leu Tyr Asn Ile Ala Gln Asp Ile Ser
            420                 425                 430

Glu Asp Asn Asp Ile Ser Ala Gln His Pro Asp Ile Leu Arg Asp Met
            435                 440                 445

Val Ser Ser Met Glu Ser Trp Ser Trp Asn Asn Gln Pro Lys Trp
450                 455                 460

Phe His Gln Ser Ala Glu Gly Ala Gln Trp Arg Leu Lys Ala Met Pro
465                 470                 475                 480

Arg Phe Asp Gln Thr Phe Gln Val Gly Asp Asn Thr Arg Ser Asn Ser
                485                 490                 495

Lys Lys Gly His
            500

<210> SEQ ID NO 5
<211> LENGTH: 11
<212> TYPE: PRT
<213> ORGANISM: Pseudoalteromonas atlantica
<220> FEATURE:
<221> NAME/KEY: MISC_FEATURE
<222> LOCATION: (1)..(1)
<223> OTHER INFORMATION: Xaa is C or S
<220> FEATURE:

```
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid, preferably S
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid, preferably L
<220> FEATURE:
<221> NAME/KEY: MISC_FEATURE
<222> LOCATION: (10)..(10)
<223> OTHER INFORMATION: Xaa is any amino acid, preferably G
<220> FEATURE:
<221> NAME/KEY: MISC_FEATURE
<222> LOCATION: (11)..(11)
<223> OTHER INFORMATION: Xaa is any amino acid, preferably R

<400> SEQUENCE: 5

Xaa Xaa Pro Xaa Arg Xaa Xaa Xaa Xaa Xaa Xaa
1               5                   10

<210> SEQ ID NO 6
<211> LENGTH: 12
<212> TYPE: PRT
<213> ORGANISM: Pseudoalteromonas atlantica
<220> FEATURE:
<221> NAME/KEY: MISC_FEATURE
<222> LOCATION: (2)..(2)
<223> OTHER INFORMATION: Xaa is Y or V
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is S or T
<220> FEATURE:
<221> NAME/KEY: MISC_FEATURE
<222> LOCATION: (5)..(7)
<223> OTHER INFORMATION: Xaa is any amino acid
<220> FEATURE:
<221> NAME/KEY: MISC_FEATURE
<222> LOCATION: (10)..(11)
<223> OTHER INFORMATION: Xaa is any amino acid

<400> SEQUENCE: 6

Gly Xaa Xaa Xaa Xaa Xaa Xaa Gly Lys Xaa Xaa His
1               5                   10
```

The invention claimed is:

1. A method for transforming iota-carrageenan to alpha-carrageenan comprising: the enzymatic catalysis of a conversion of an iota-carrabiose motif to an alpha-carrabiose motif by an enzyme whose peptide sequence comprises the peptides having the following sequences:

NGQFDNTVIVFTSDNGGK, (SEQ ID NO: 1)

FDQTFQVGDNTR, (SEQ ID NO: 2)

and

ETEYITDGLSR; (SEQ ID NO: 3)

and configured to transform iota-carrageenan to alpha-carrageenan.

2. The method as claimed in claim 1, in which the peptide sequence of the enzyme is (SEQ ID NO: 4)
MTFNKKVSTLLWGTLIAISVGNASAADAGQSKADESNEKPNILFVLA

DDLGYNDVGFNGSTDIKTPNLDGLAKNGMTFDAAYVAHPFCGPSRAA

IMTGRYPHKIGAQFNLPEDNSNVGVSADELFIAQTMKSAGYFTGAMG

KWHLGEASEYHPNKHGFDEFYGFLGGGHNYFPEQFEAAYNKRVAQGM

TNINMYLTPLEHNGKEVRETEYITDGLSREAVNFVDKAAAKKKPFFL

-continued

```
YLAYNAPHVPLQAKEEDMAMFSQIKDKKRRTYAGMVYAVDRGVGRIV

EQLKKNGQFDNTVIVFTSDNGGKLGQGANNYPLKEGKGSVQEGGFRT

PMLVHWPKHMKAGSRFSHPVLALDLYPTFAGLGGAVLPEDKKLDGKD

IWADIQANTAPHKDEFIYVLRHRNGYSDAAARRNQFKAVKNHNDDWK

LYNIAQDISEDNDISAQHPDILRDMVSSMESWSWNNQQPKWFHQSAE

GAQWRLKAMPRFDQTFQVGDNTRSNSKKGH.
```

3. The method as claimed in claim 1, in which said enzyme is a 4S-iota-carrageenan sulfatase.

4. The method as claimed in claim 1, in which the enzyme is produced by a host cell comprising a nucleic acid encoding said enzyme and/or a vector comprising a nucleic acid sequence encoding said enzyme.

* * * * *